US006994249B2

(12) United States Patent
Peterka et al.

(10) Patent No.: US 6,994,249 B2
(45) Date of Patent: Feb. 7, 2006

(54) SYSTEM AND METHOD FOR DRUG MANAGEMENT UTILIZING TRANSFERABLE LABELS

(75) Inventors: Michael Anthony Peterka, Mequon, WI (US); James Robert Martin, Powell, OH (US)

(73) Assignee: Cardinal Health Technologies, LLC, Las Vegas, NV (US)

( * ) Notice: Subject to any disclaimer, the term of this patent is extended or adjusted under 35 U.S.C. 154(b) by 200 days.

(21) Appl. No.: 10/445,792

(22) Filed: May 27, 2003

(65) Prior Publication Data

US 2004/0243434 A1 Dec. 2, 2004

(51) Int. Cl.
    *G06F 17/00* (2006.01)
(52) U.S. Cl. ............... 235/375; 235/376; 235/462.01; 705/3; 283/81
(58) Field of Classification Search ............... 235/375, 235/461.09, 462.01, 462.09; 705/3; 283/81
    See application file for complete search history.

(56) References Cited

U.S. PATENT DOCUMENTS

| | | | | |
|---|---|---|---|---|
| 4,857,713 A | | 8/1989 | Brown | 235/375 |
| 4,857,716 A | * | 8/1989 | Gombrich et al. | 235/375 |
| 5,118,369 A | | 6/1992 | Shamir | 156/64 |
| 5,129,974 A | | 7/1992 | Aurenius | 156/64 |
| 5,445,271 A | * | 8/1995 | Kakizaki et al. | 206/459.5 |
| 5,597,995 A | | 1/1997 | Williams et al. | 235/375 |
| 5,692,640 A | * | 12/1997 | Caulfield et al. | 221/70 |
| 5,700,998 A | | 12/1997 | Palti | 235/375 |
| 5,752,723 A | * | 5/1998 | Robertson | 283/67 |
| 5,845,264 A | | 12/1998 | Nellhaus | 705/28 |
| 5,964,374 A | | 10/1999 | Yuyama et al. | 221/17 |
| 5,992,742 A | | 11/1999 | Sullivan et al. | 235/462.01 |
| 6,016,618 A | * | 1/2000 | Attia et al. | 40/633 |
| 6,032,155 A | | 2/2000 | de la Huerga | 707/104 |
| 6,170,746 B1 | | 1/2001 | Brook et al. | 235/385 |
| 6,202,158 B1 | * | 3/2001 | Urano et al. | 713/201 |
| 6,244,764 B1 | * | 6/2001 | Lei et al. | 400/103 |
| 6,446,868 B1 | * | 9/2002 | Robertson et al. | 235/462.1 |
| 6,519,569 B1 | * | 2/2003 | White et al. | 705/3 |
| 6,671,563 B1 | * | 12/2003 | Engelson et al. | 700/2 |
| 2003/0009244 A1 | | 1/2003 | Engleson et al. | 700/86 |

* cited by examiner

*Primary Examiner*—Thien M. Le
*Assistant Examiner*—Seung H Lee
(74) *Attorney, Agent, or Firm*—Donald O. Nickey; Gallagher & Dawsey

(57) ABSTRACT

A system and method for drug management using transferable labels provides a chain of identity for medications from their arrival in a pharmacy to administration to a patient. Drug information is read, in some embodiments optically, and imprinted on a transferable label optionally fabricated of low stretch, chemical resistant material, that is attached to the medication package. The transferable label is checked to make sure that it correctly corresponds to the drug information. At the time of preparation for administration, the transferable label is transferred from the medication package to the administration device, typically a syringe or dose cup. The health care giver scans the patient identification information, usually found on an identification bracelet, the transferable label, and optionally, a unique code belonging to the administering party. The system will reject non-matches between scanned inputs, and may be configured with a variety of safety steps, displays, and reports.

15 Claims, 6 Drawing Sheets

SYSTEM AND METHOD FOR DRUG MANAGEMENT UTILIZING TRANSFERABLE LABELS

TECHNICAL FIELD

The instant invention relates to a method and system for identifying prescribed medication for a patient, particularly a method of utilizing transferable machine readable labels in a drug management system to improve safety.

BACKGROUND OF THE INVENTION

The United States Food and Drug Administration estimates that approximately 1.3 million people in the United States are accidentally injured each year by medical therapy, 98,000 fatally. One study estimated the cost of treating patients suffering adverse drug effects to be nearly $4.5 billion annually. One type of adverse drug event, and one of the most tragic, is an error in administration, where the wrong drug or wrong dosage of the right drug is administered to a patient.

At least one study has shown that patients are in greatest danger of being exposed to a medication administration error during the first 48 hours of admission to a health care facility and within the first 48 hours after prescription of a new drug. These are precisely the times when staff and patients are both least likely to be familiar with the correct drugs, dosages, and treatment regimens appropriate for the individual. This highlights the need for fail-safe systems that reduce the possibilities of human error during drug administration.

Simple labeling of drug packages with printed indicia has progressed to coding of items as small as unit dose containers, or even single pills and capsules, with machine readable code, as seen for example, in U.S. Pat. No. 5,700,998 to Palti. This patent discloses a method of bar coding individual tablets and capsules. Such individual bar codes can be read by systems such as that seen in U.S. Pat. No. 4,857,713 to Brown.

A number of methods incorporate such coding as part of patient safety systems. For example, U.S. Pat. No. 4,857,713 to Brown discloses a system that both reads patient identification bands and medication unit dose bar codes, and interacts with a patient history file and a physician instruction file in a host computer, and a transaction file and an instruction file in a portable computer. The system compares the bar codes on the medication with the patient's identification, doctor's orders, and other database items.

However, all these systems pose two problems. First, a small bar code is often limited in the amount of information it can carry. Such coding of drugs traditionally identifies only limited information about the drug identity and the dosage. If additional patient or drug information is desired to be coded, a larger individualized bar code must be generated and attached to the medication in some fashion. Second, previous systems assume that a machine readable bar code is present on the unit dose packaging or on the medication itself, at all critical stages in the route of administration from prescription to patient. This has been difficult or impossible to achieve, until now, with a large class of medications, namely, those that are supplied in a liquid form, or in a powdered form for use with a diluent, where the medication must be drawn into a patient administration device. The prototypical example of this class is a liquid drug dispensed in a small ampule or vial, which must be opened, the contents of which are drawn into a syringe, and then administered to a patient. As an initial matter, the very small size of such ampules makes it difficult to bar code them. This small amount of space is further limited by the fact that the ampule labeling must not be covered by the bar code. Even if a bar code is attachable to an ampule, the small size limits most bar codes to very rudimentary information. Lastly, conventional bar codes placed on the ampule are not transferable, and therefore are detached from the medication as soon as the drug is dispensed into a syringe or other patient administration vehicle. This creates a potentially hazardous break in the chain of tracking of drugs from dispensing unit to patient administration.

Drugs are frequently opened or compounded in a pharmacy, drawn into syringes, and then transferred to a patient care unit. Alternatively, they are often prepared in a preparation area adjacent to a patient's room. Accordingly, there is a break in the chain of coding between pharmacy and eventual administration. The syringes or other patient administration devices may be placed into bar code labeled bags, or such similar carrier, but at all stages after the drug is placed into the syringe, there is an ever present danger that the drug will be separated from the labeling. Accordingly, there is a continuous danger of patient dosing mishaps.

The instant invention solves both of these shortcomings of previous bar code systems by providing a small bar code that can be custom printed to individual patients and their medications, and transferred from medication ampules or other small containers onto patient administration devices such as syringes or dose cups, thereby allowing medication to be accurately tracked and checked at any and all points between prescribing and administration.

SUMMARY OF THE INVENTION

The instant invention relates to a novel method and system for increasing the security of drug administration by providing a positive chain of identity from the time a drug is received by a health care facility to the time that it is administered to a patient.

The method and system is designed to provide a transferable label that is attached to the medication and transferred from the manufacturer packaging onto a syringe or a dose cup. The system provides for a computer system containing a plurality of patient and drug information networked with a plurality of input devices, along with optional display devices, and a means for imprinting transferable labels bearing machine readable code.

In accordance with the present invention, medications are received in their manufacturer's packaging at a pharmacy or other receiving area. Such medications will either bear a manufacturer supplied machine readable code, or visually readable indicia identifying the medication. Medications bearing a manufacturer supplied machine readable code are scanned, and a transferable label corresponding to the optically read drug information is generated and affixed to the packaging. Given the capacity of the transferable label, in some embodiments of the instant invention, to bear large amounts of machine readable code, information encoded on the transferable label may not necessarily be restricted to drug information, and may include individualized patient, or other, information. Medications not bearing a manufacturer supplied machine readable label have the information from their readable indicia input into the computer system, and a transferable label corresponding to the input drug information is generated and affixed to the packaging.

The transferable labels may incorporate many embodiments, including codes capable of conveying large amounts of information, codes containing error correction protocols, tabbing to ease placement of the labels, adhesive backing allowing multiple adhesion-removal cycles, and fabrication from materials designed to resist stretch and also to resist common chemicals found in health care environments.

After a safety check to make sure that the medication packaging matches the information imprinted on the transferable label, the drugs are released to a preparation area. As the drugs are dispensed into a variety of patient administration vehicles, such as syringes and dose cups, the transferable labels are removed from the medication packages and transferred to the administration vehicles. This maintains a chain of identity from the pharmacy or other dispensing area to the patient.

At the time of administration, the health care giver intending to administer the information must scan patient identification information from a patient identification device, scan the transferable label, and optionally scan their own identity information, before securing permission from the system to administer the medication. The system is capable of various alarms, displays, reports and may contain safety enhancing embodiments to discourage attempts to circumvent the system.

Thus, there is disclosed a method for drug management using transferable labels, the method comprising the steps of providing a medication package containing at least one medication and primary information; applying a transferable label containing transferable label information expressed as machine readable code to the medication package, the transferable label information being relative to the medication; scanning the transferable label with a drug information collection unit adapted to obtain the transferable label information from the transferable label; communicating the transferable label information from the drug information collection unit to a computer system; comparing the transferable label information and primary information obtained from the medication package; preparing the medication for final administration in a patient administration vehicle if the transferable label information corresponds to the primary information; transferring the transferable label from the medication package to the patient administration vehicle; scanning a patient identification device with a data collection unit adapted to obtain patient identification information from the patient identification device and the transferable label; scanning the transferable label with the data collection unit to obtain the transferable label information; comparing the patient identification information and the transferable label information; and administering the medication if the patient identification information corresponds to the transferable label information.

There is also disclosed a system for drug management using transferable labels, the system comprising a computer system containing at least one unique patient medical history file and a plurality of medication information relative for each of a plurality of predetermined drugs; a plurality of input means capable of receiving a plurality of information and communicating with the computer system; a plurality of display means capable of displaying any of the plurality of information and communicating with the computer system; at least one printer in communication with the computer system and capable of printing a transferable label containing transferable label information expressed as machine readable code corresponding to the information relative to the medication; at least one transferable label, imprinted with the machine readable code; and a patient administration vehicle for delivery of the medication to a patient.

There is further disclosed a method for drug management using transferable labels, the method comprising the steps of providing a medication package containing at least one medication; applying a transferable label containing transferable label information expressed as machine readable code to the medication package, the transferable label information being at least relative to the medication; scanning the transferable label with a drug information collection unit adapted to obtain the transferable label information from the transferable label; communicating the transferable label information from the drug information collection unit to a computer system; comparing the transferable label information and primary information obtained from the medication package; preparing the medication for final administration in a patient administration vehicle if the transferable label information corresponds to the primary information; transferring the transferable label from the medication package to the patient administration vehicle; scanning a patient identification device with a data collection unit adapted to obtain patient identification information from the patient identification device and the transferable label; communicating the patient identification information to the computer system and associating the patient identification information to at least one unique patient medical history file; scanning the transferable label with the data collection unit to obtain the transferable label information; displaying on at least one display device at least a portion of the information contained in the computer system; comparing the patient identification information and the transferable label information; and administering the medication if the patient identification information corresponds to the transferable label information.

BRIEF DESCRIPTION OF THE DRAWINGS

Without limiting the scope of the present invention as claimed below and referring now to the drawings and figures:

DETAILED DESCRIPTION OF THE DRAWINGS

The system and method for drug management utilizing transferable labels of the instant invention enables a significant advance in the state of the art. The preferred embodiments of the apparatus accomplish this by new and novel arrangements of elements that are configured in unique and novel ways and which demonstrate previously unavailable but desirable capabilities.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Figure 1:
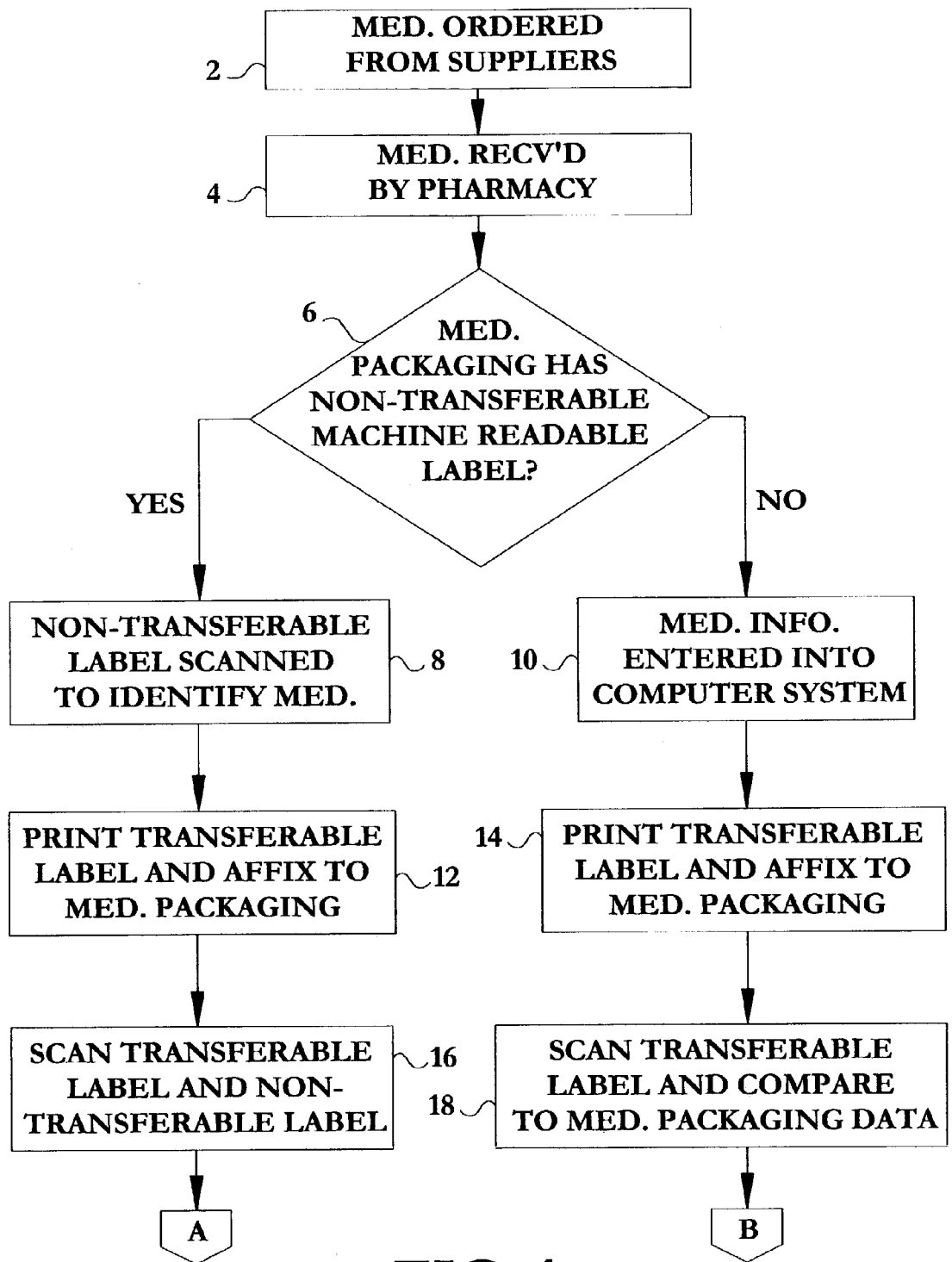
FIGS. 1 through 3 form a flow chart illustrating an embodiment of the method for drug management utilizing transferable labels of the present invention.
Figure 6:
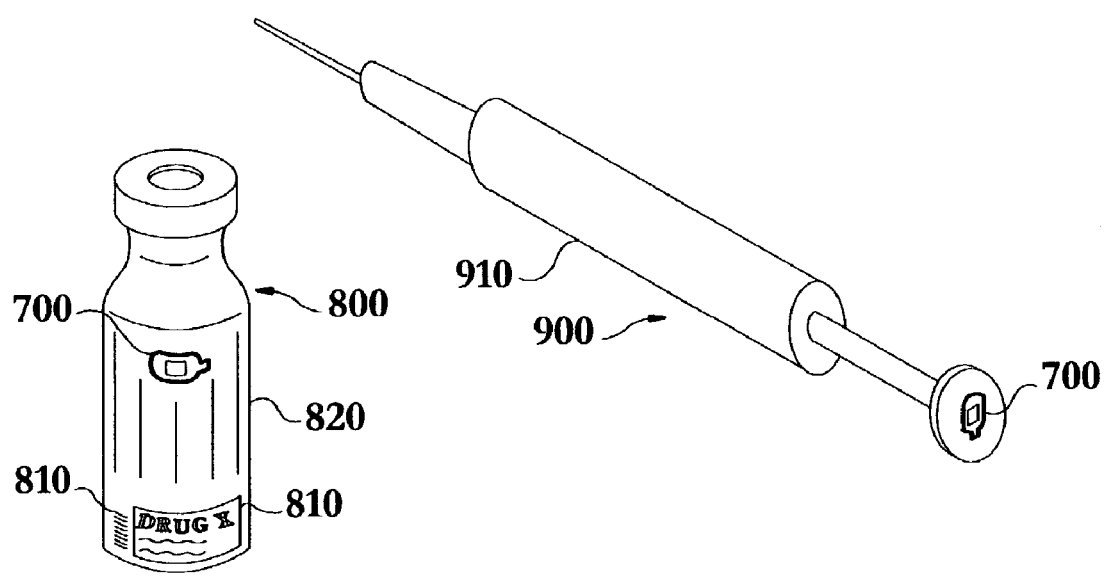
FIG. 6 shows an elevated perspective view, not to scale, of the transferable label of FIG. 5 in an embodiment for an injectable medication, illustrating the transferable label affixed to a medication package in the form of a drug vial and a patient administration vehicle in the form of a needle tipped syringe.
Figure 7:
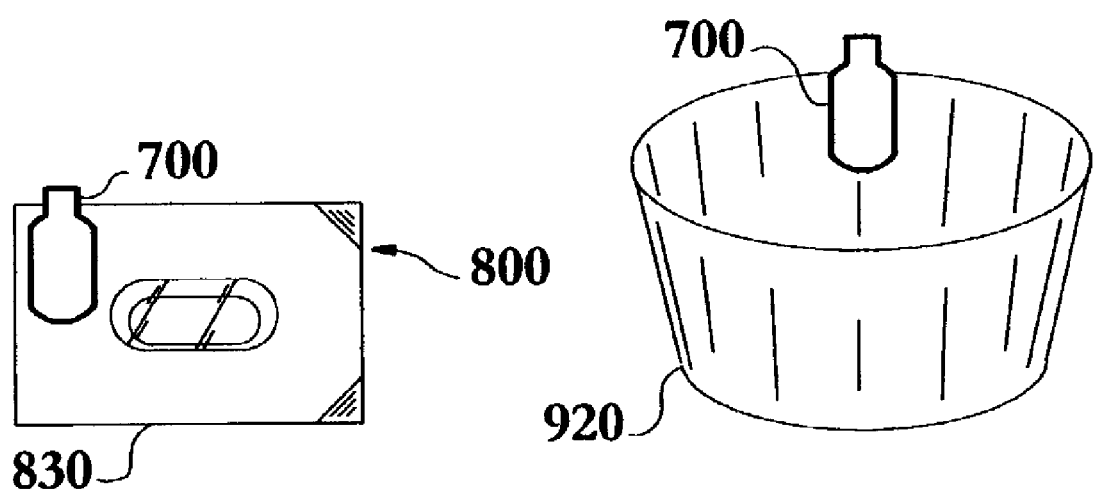
FIG. 7 shows an elevated perspective view, not to scale, of the transferable label of FIG. 5 in an embodiment for orally administered medication, illustrating the transferable label attached to a medication package in the form of a blister package and a patient administration vehicle in the form of a dose cup.

Referring generally to FIGS. 1 through 7, in one form, the instant invention comprises a method and system for employing a computer system 200 containing at least one unique patient medical information file and a plurality of medication information relative for each of a plurality of predetermined drugs. The method of drug management utilizes transferable labels 700, seen in FIG. 5, with the method beginning, as seen in FIG. 1, with the steps of providing a medication package 800 containing at least one medication. Typical medication packages 800 might include, by way of example and not limitation, vials 820 for injectable medications, and blister packages 830 for orally administered medications, as seen in FIGS. 6 and 7. As seen in FIG. 1, medications are ordered from suppliers 2 and are received in a pharmacy 4 or other receiving unit. Medications will be of two types that are initially separated 6 by the system: those having a non-transferable machine readable label providing primary information 810 as part of the medication package 800 and those that do not. Those that do not have a non-transferable machine readable label will have visually discernable human language labeling. In either case, the primary information 810, as seen in FIG. 6, may be as simple as the name and strength of the drug, or may be more complex and have additional information such as product expiration date and lot number.

Next, the method comprises the step of applying a transferable label 700 containing machine readable information 710 to the medication package 800, the transferable label information being relative to the medication. The system may utilize a variety of input means capable of receiving a plurality of information and communicating with the computer system 200 in generating the transferable labels 700. Those medication packages 800 having a non-transferable machine readable label are scanned 8 with a drug information collection unit 310 and a transferable label 700 is printed, by a printer 500 in communication with the computer system 200 and capable of printing machine readable code corresponding to the information relative to the medication, with machine readable code 710 and affixed 12 to the medication package 800. Those medication packages 800 not having a non-transferable machine readable label have their primary information 810 input 10 into the computer system 200 and a transferable label 700 is printed containing machine readable code 710 and affixed 14 to the medication package 800. Such input can be accomplished by such means as, by way of example and not limitation, an alphanumeric input device 320 such as a keyboard, and by a computer mouse 330. The transferable label 700 may be affixed to the medication package as an adjunct step by the printer 500, or by a separate process, including manual transfer.

The function of the transferable label 700 may be enhanced by various embodiments. The utilization of a data matrix code enhances the amount of information that may be contained on the transferable label 700. For example, a 2D datamatrix code is able to contain up to 2335 characters in a 0.72 inch (1.8 cm) square, i.e., a square having sides 0.72 inches, or 1.8 centimeters, in length. A preferable embodiment includes a transferable label having an area of less than approximately 0.25 in$^2$ (0.64 cm$^2$) with a machine readable code having an area of less than approximately 0.2 in$^2$ (0.5 cm$^2$). Various error correction protocols may be employed, allowing for correct scanning with up to 50% of the code damaged. The transferable label 700 may be shaped as tabbed label for easy placement and removal with the finger tips and may have an adhesive backing capable of multiple adhesion-removal cycles. The material of the transferable label 700 may be fabricated from a low stretch material, such as, by ways of example and not limitation, polypropylene, such that mechanical stresses associated with placement and removal of the transferable label 700 do not tend to stretch the label, and thereby damage the readability of the code. Additionally, the transferable label 700 material may be fabricated from materials resistant to common solvents found in health care settings, such as, by way of example and not limitation, alcohol and povidone-iodine solutions.

Figure 2:
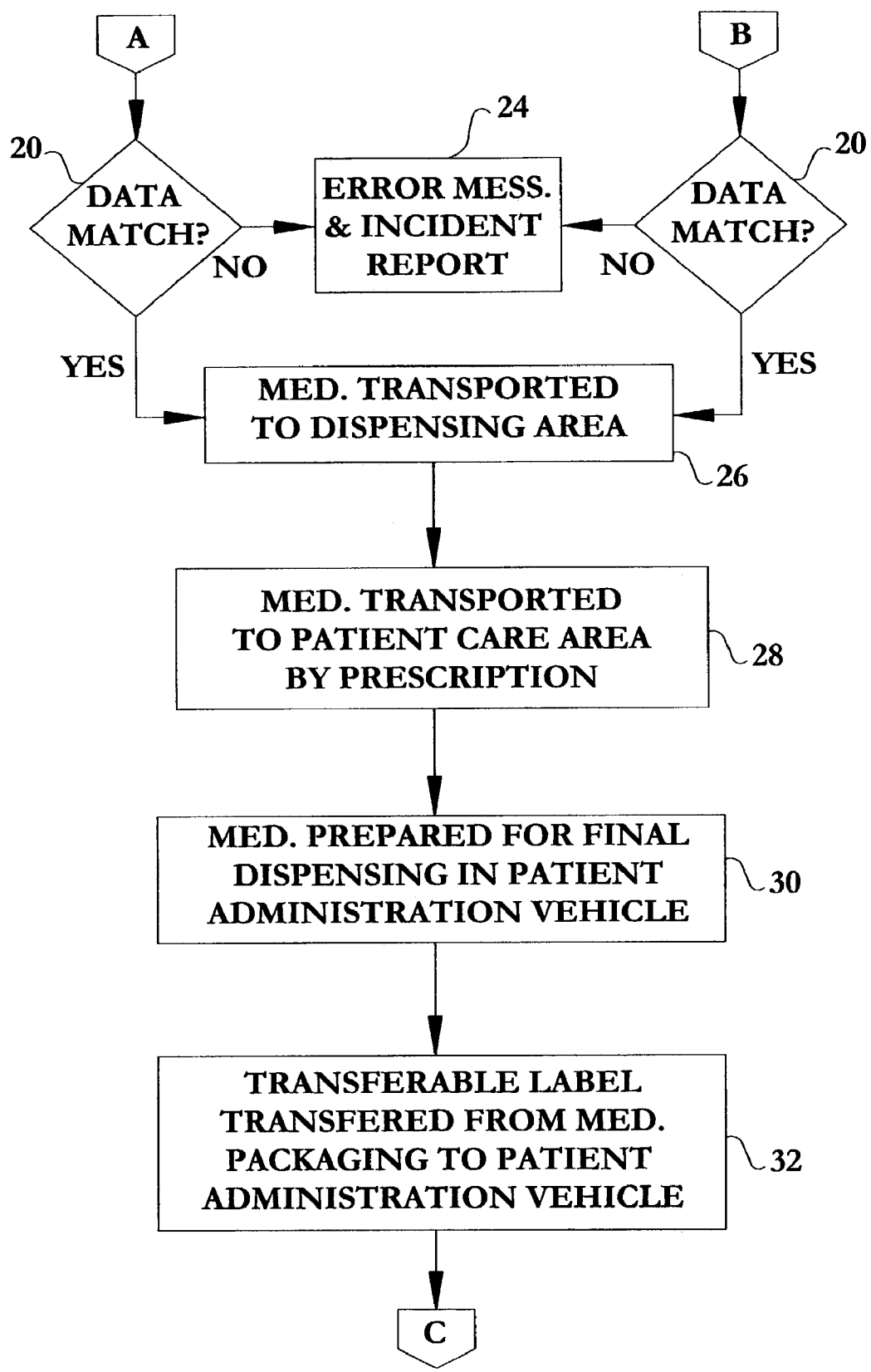

The method proceeds, as seen in FIG. 1, by scanning the transferable label 700 with a drug information collection unit 310 adapted to obtain the transferable label information from the transferable label 700 and communicating the transferable label information from the drug information collection unit 310 to a computer system 200, which compares the transferable label information and primary information 810 obtained from the medication package 800. Regardless of whether the medication package 800 had a non-transferable machine readable label or whether the primary information 810 was otherwise input into the computer system 200, an important step in the method is this comparing 20, seen in FIG. 2, of the medication package 800 primary information 810 with the machine readable code 710 imprinted on the transferable label 700. In the case of those medications where the medication package 800 had a non-transferable machine readable label, that label is again scanned 16 with a drug information collection unit 310 and the machine readable code 710 of the transferable label 700 is scanned 16 with a data collection unit 340 and the information derived from the two scans are compared 20, as seen in FIG. 2. The drug information collection unit 310 and the data collection unit 340 may be part of the same scanning device or may be configured as separate devices.

In the case of those medications where the medication package 800 did not have a non-transferable machine readable label, the machine readable code 710 of the transferable label 700 is scanned 18 with a drug information collection unit 310 and the scan of the transferable label 700 is compared 20 to the primary information 810 as displayed on the medication packaging 800, as also seen in FIG. 2.

If the transferable label information corresponds to the primary information 810 and the comparing therefore results in a match 20, seen again in FIG. 2, the medication is released and transported to the dispensing area 26. In the case of non-agreement, an error message may be produced and an incident report may be generated 24, and the medication is not released.

Released medication is then transported to a patient care area by prescription 28 and prepared 30 for final administration in a patient administration vehicle 900, and the transferable label 700 is transferred 32 from the medication package 800 to the patient administration vehicle 900, as seen in FIGS. 6 and 7. Typical administration vehicles might include, but are not limited to, syringes 910 for injectable medications, and dose cups 920 for orally administered medications. It is at this point in the current state of the art that the usual chain of identity between labeled medication and medication ready for administration is broken. In a prototypical example, medication is drawn from a labeled vial 820 into an unlabelled syringe 910. There is, in current state of the art, no practical way of transferring the label from the vial 820 to the syringe 910, and so a variety of ad hoc methods, such as hand labeling, attaching the vial 820 to the syringe 910 with tape, and others, are typically employed to try to keep track of the nature of the drug in the syringe 910. Such measures are of limited utility, and are failure prone.

In the present invention, there can be a near seamless movement of the transferable label 700 from a medication package 800 to a patient administration vehicle 900. Typical combinations of a medication package 800 and a patient administration vehicle 900 are seen in FIG. 6, showing a drug vial 810 bearing a transferable label 700 and a needle tipped syringe 900 bearing a transferred label 700. Also shown in FIG. 7, is a blister package 830 bearing a transferable label 700 and a dose cup 920, also bearing the transferable label.

Figure 3:
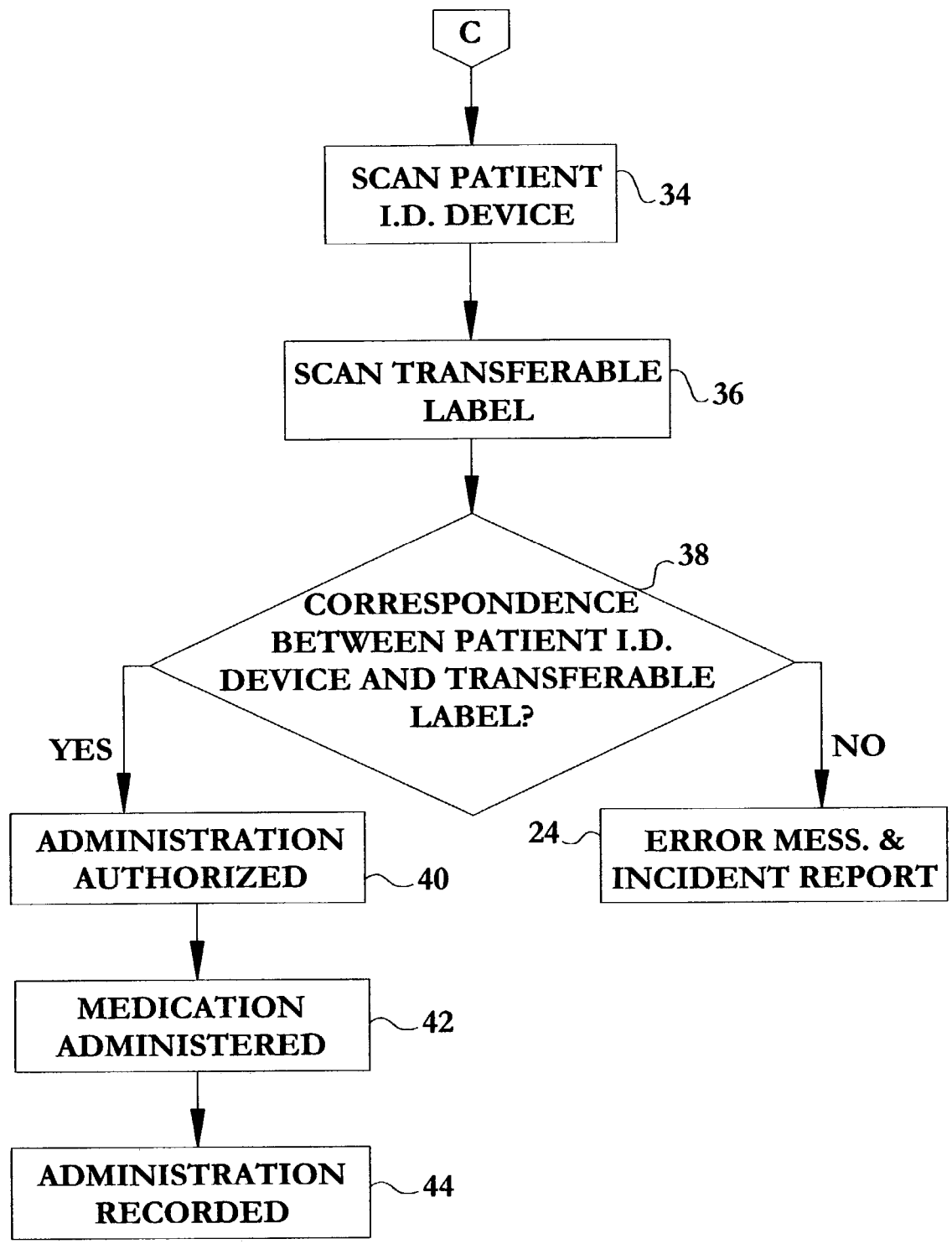

At the time of administration, as seen now in FIG. 3, the method includes scanning a patient identification device 34 with a data collection unit 340 adapted to obtain patient identification information from both a patient identification device and the transferable label 700, then scanning 36 the transferable label 700 with the data collection unit 340 to obtain the transferable label information. Typical patient identification devices might include, but are not limited to, a tamper-evident bracelet or band bearing predetermined indicia. If comparing 38 the patient identification information and the transferable label information produces correspondence, administration is authorized 40, and the medication may be administered 42 and recorded 44.

As also seen in FIG. 3, if comparing results in non-agreement following scanning 34 the patient identification device and scanning 36 the transferable label 700, administration is not authorized and the method may generate in an error message and incident report 24.

The utility of the computer system 200 and network 600 in enhancing patient care and safety will be appreciated in many ways by one skilled in the art. The step of comparing the patient identification information and the transferable label information may also include communicating the patient identification information and the transferable label identification to the computer system 200, and recording the administration 42 of the medication in the data collection unit 340 and communicating the administration 42 to the computer system 200.

For example, the network 600 may communicate the patient identification information to the computer system 200 and associate the patient identification information to at least one unique patient medical history file. This would allow for cross checking medications against a patient's medical history, history of allergies, drug interactions, dosage regimes, and virtually any other quantifiable patient or drug information that may be gathered and contained in the computer system 200. The network connecting various components of the computer system 200 may be wireless or wired.

Collection and processing of information on health care givers may also be incorporated into the method. For example, the method may further include the step of scanning at least one administration identification device with the data collection unit 340, adapted to obtain administration identification information from a health care giver. Such administration identification information may include the personal identity and other credentials of the health care giver, and the administration identification device may comprise any machine readable code, such as a bar code, and may be incorporated into any unique personal indicia, such as the identification badge of the health care provider. The data collection unit 340 may communicate the administration identification information to the computer system 200. As one example, the computer system 200 may authorize a wider range of health care givers to administer certain medications, namely those having a lower risk of adverse effects. The administration of more dangerous medications may be restricted to those having enhanced access. Health care givers may be restricted to administering drugs to certain patients, organized by identity or location, or to administration on certain patient care units, or at certain predetermined times, or according to any other quantifiable scheme.

Security can be further enhanced by imposing a time limit between scans of the patient identification device and the administration identification device; that is, requiring that one proposing to administer a medication scan their own and the patient's information within a predetermined time limit. In such a refinement, the method may include the step of scanning the at least one administration identification device with the data collection unit 340, and also require scanning the patient identification device within a predetermined amount of time of scanning the at least one administration identification device. The data collection unit 340 may communicate the administration identification information to the computer system 200, and deny access to the patient medical history file if the time between scans of the patient identification device and the administration identification device exceeds a predetermined time limit. Such a step would tend to discourage health care givers from scanning their administration identification device and then handing off the medication to another person for administration.

One skilled in the art will also readily see that a variety of other refinements may be utilized as part of the method and system. For example, further including the step of comparing the transferable label information and the patient medical history file and then generating and displaying a warning message if comparing produces non-agreement, will tend to decrease the incidence of medication errors. As noted above, health care givers can be incorporated into the method of the instant invention, by further including the step of comparing the transferable label information, the patient medical history file, and the administration identification information. The method might then generate and display a warning message if comparing produces non-agreement between any two of the transferable label information, the patient medical history file, and the administration identification information.

Figure 4:
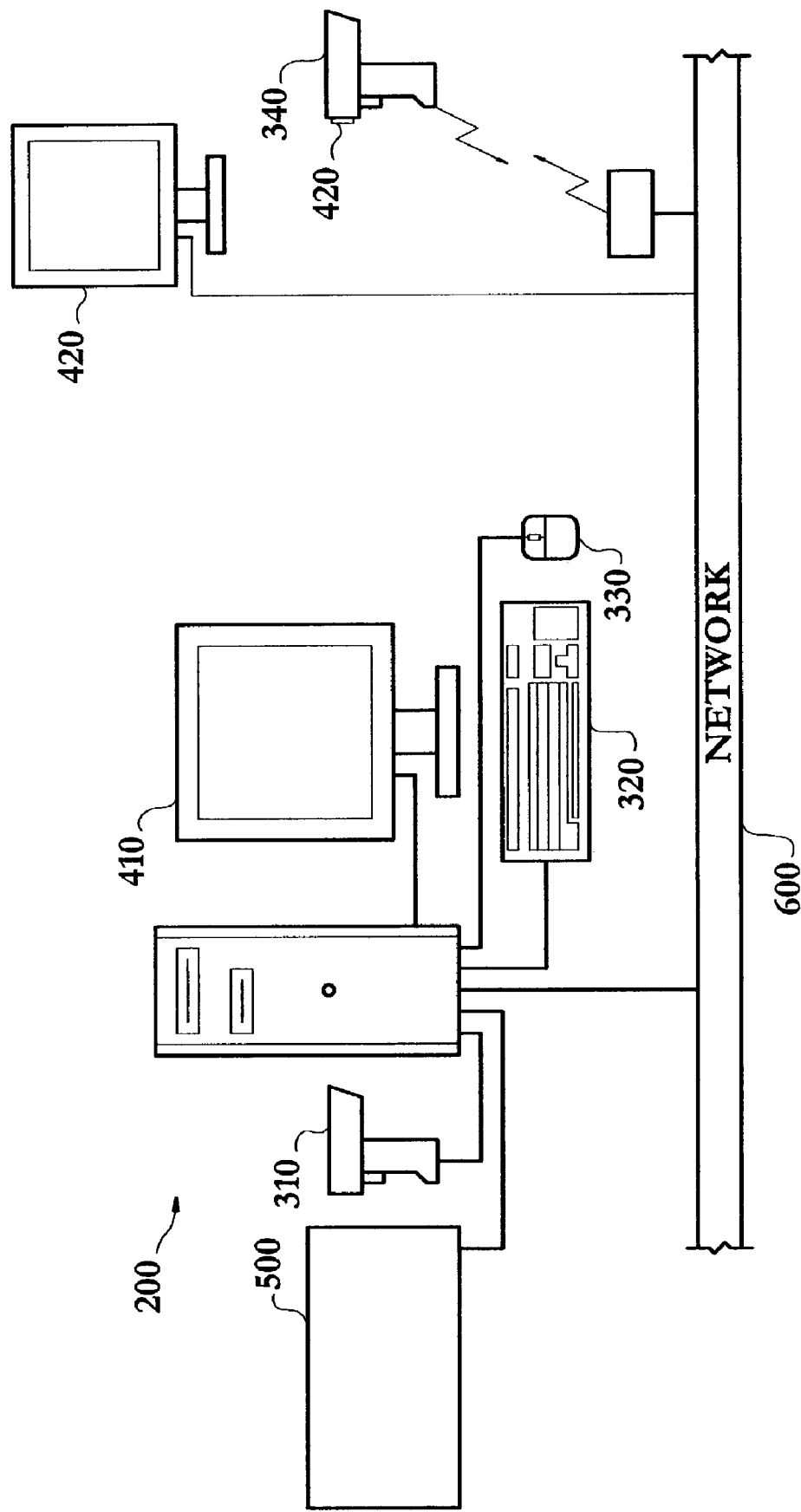
FIG. 4 shows a block diagram of an embodiment of the system for drug management utilizing transferable labels of the present invention.
Figure 5:
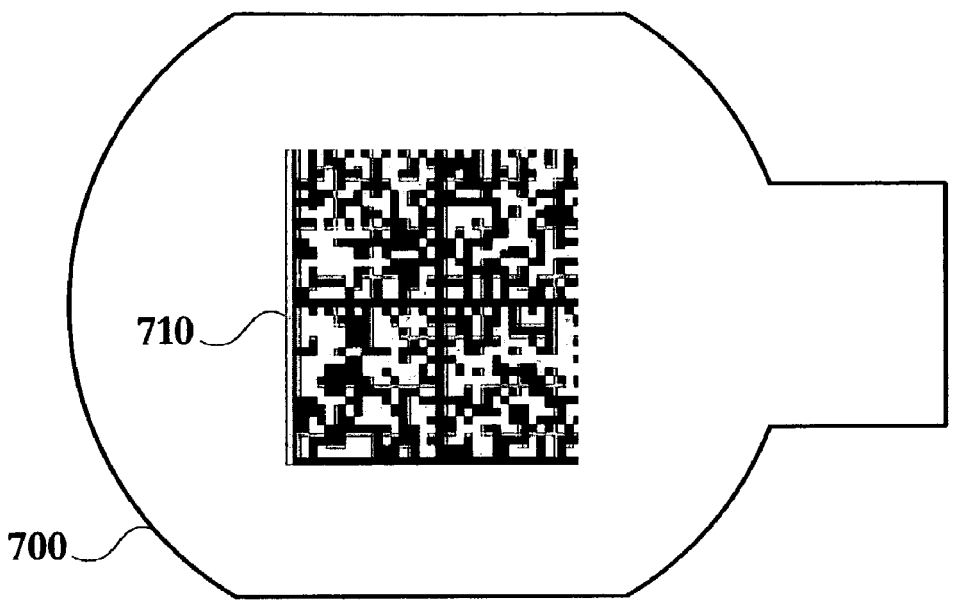
FIG. 5 shows a top plan view, not to scale, of the transferable label of the present invention.

A wide variety of display devices, capable of displaying any of the plurality of information and communicating with the computer system 200, may be adapted to this system. Such display devices might include, but are not limited to, monitors 410 or other local displays 420, such as audible, visual, or tactile alarms; at many points in the method. Display devices may be built into input devices such as the drug information collection unit 310 or the data collection unit 340, as seen in FIG. 4. Display devices may be distinct from input devices yet be physically closely associated, as for example, a monitor 410 placed adjacent to a computer mouse 330, as also seen in FIG. 4. Display devices may also be distant from the actual medication preparation and administration areas, for example, supervisors may be able to monitor individual patients, health care givers, patient care units, or medication preparation areas from their offices or other locations.

The method may be used to generate a wide variety of reports, including, but not limited to, incident reports of non-agreement of scans, billing information, pharmacy orders, individual patient reports, and assessment of individual health care givers.

The method may also have a self-disabling feature if certain critical events are reported. For example, the method may further comprise the step of denying access to the unique patient medical history file following the generation of an incident report, the access being capable of restoration only by authorized personnel. Such a "lock out" would require that a supervisory person re-initiate patient access, and presumably investigate the precipitating circumstances of such a "lock out," before the system would authorize any further medication administration to a an individual patient, or even a group of patients.

Numerous alterations, modifications, and variations of the preferred embodiments disclosed herein will be apparent to those skilled in the art and they are all anticipated and contemplated to be within the scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations.

Accordingly, even though only few variations of the present invention are described herein, it is to be understood that the practice of such additional modifications and variations and the equivalents thereof, are within the spirit and scope of the invention as defined in the following claims.

INDUSTRIAL APPLICABILITY

The system and method answers a long felt need for increasing safety in the administration of medication by providing a practical means for maintaining a chain of identity of a medication from the time it is received in a pharmacy or other receiving area to the time that it is administered to a patient. The apparatus provides a transferable label that moves, attached to the medication, along with the medication through the various transport steps involved in delivering a medication to a patient.

We claim:

1. A method for drug management using transferable labels, the method comprising the steps of:
   providing a medication package containing at least one medication and primary information;
   applying a transferable label containing transferable label information expressed as machine readable code to the medication package, the transferable label information being at least relative to the medication;
   scanning the transferable label with a drug information collection unit adapted to obtain the transferable label information from the transferable label;
   communicating the transferable label information from the drug information collection unit to a computer system;
   comparing the transferable label information and primary information obtained from the medication package;
   preparing the medication for final administration in a patient administration vehicle if the transferable label information corresponds to the primary information;
   transferring the transferable label from the medication package to the patient administration vehicle;
   scanning a patient identification device with a data collection unit adapted to obtain patient identification information from the patient identification device and communicating the patient identification information to the computer system and associating the patient identification information to at least one unique patient medical history file;
   scanning the transferable label with the data collection unit to obtain the transferable label information;
   comparing the patient identification information and the transferable label information; further comprising the steps of scanning at least one administration identification device with the data collection unit, further adapted to obtain administration identification information, within a predetermined amount of time of scanning the patient identification device and communicating the administration identification information to the computer system and denying access to the patient medical history file if the time between the scanning of the patient identification device and the administration identification device exceeds the predetermined time limit;
   comparing the transferable label information, the patient medical history file, and the administration identification information;
   generating and displaying a warning message on at least one warning device in communication with the computer system if comparing produces non-agreement between any two of the transferable label information, the patient medical history file, and the administration identification information and denying access to the unique patient medical history file following the generation of the warning message, the access being capable of restoration only by an authorized person; and
   administering the medication if the patient identification information corresponds to the transferable label information and the time between the scanning of the patient identification device and the administration identification device does not exceed the predetermined time limit and no non-agreement between any two of the transferable label information, the patient medical history file, and the administration identification information has been detected.

2. The method of claim 1, further including the step of generating an incident report in communication with the computer system if comparing produces non-agreement between any two of the transferable label information, the patient medical history file, and the administration identification information.

3. A system for drug management using transferable labels, the system comprising:
   a computer system containing at least one unique patient medical history file and a plurality of medication information relative for each of a plurality of predetermined drugs;
   a plurality of input means capable of receiving a plurality of information and communicating with the computer system;
   a plurality of display means capable of displaying any of the plurality of information and communicating with the computer system;
   a report generating means in communication with the computer system and capable of generating at least an incident report;

means for scanning at least one administration identification device with a data collection unit, adapted to obtain administration identification information, within a pre-determined amount of time of scanning the patient identification device and communicating the administration identification information to the computer system;

means to deny access to the patient medical history file if the time between the scanning of the patient identification device and the administration identification device exceeds a pre-determined time limit at least one printer in communication with the computer system and capable of printing a transferable label containing transferable label information expressed as machine readable code corresponding to the information relative to the medication;

at least one transferable label, imprinted with the machine readable code; and a patient administration vehicle for delivery of the medication to a patient.

4. The system of claim 3, wherein the plurality of input means includes at least one drug information collection unit capable of reading machine readable code expressed on the transferable label.

5. The system of claim 3, wherein the printer is further capable of affixing any of the at least one transferable labels to at least one medication package.

6. The system of claim 3, wherein the machine readable code is a datamatrix code.

7. The system of claim 6, wherein the machine readable code is a 2D datamatrix code having a capacity of up to 2335 characters in a square having sides 0.72 inches in length.

8. The system of claim 3, wherein the machine readable code contains an error correction code allowing for correct scanning with up to 50% of the code damaged.

9. The system of claim 3, wherein the at least one transferable label is a shaped as a tabbed label having an adhesive backing capable of multiple adhesion-removal cycles.

10. The system of claim 3, wherein the at least one transferable label is constructed of a material substantially resistant to alcohol and povidone-iodine solutions.

11. The system of claim 3, wherein the at least one transferable label is constructed of a low stretch material.

12. The system of claim 11, wherein the low stretch material is polypropylene.

13. The system of claim 3, wherein the patient administration vehicle is a syringe.

14. The system of claim 3, wherein the patient administration vehicle is a dose cup.

15. A method for drug management using transferable labels, the method comprising the steps of:

providing a medication package containing at least one medication;

applying a transferable label containing transferable label information expressed as machine readable code to the medication package, the transferable label information being at least relative to the medication;

scanning the transferable label with a drug information collection unit adapted to obtain the transferable label information from the transferable label;

communicating the transferable label information from the drug information collection unit to a computer system;

comparing the transferable label information and primary information obtained from the medication package;

preparing the medication for final administration in a patient administration vehicle if the transferable label information corresponds to the primary information;

transferring the transferable label from the medication package to the patient administration vehicle;

scanning a patient identification device with a data collection unit adapted to obtain patient identification information from the patient identification device and the transferable label;

communicating the patient identification information to the computer system and associating the patient identification information to at least one unique patient medical history file;

scanning the transferable label with the data collection unit to obtain the transferable label information;

displaying on at least one display device at least a portion of the information contained in the computer system;

comparing the patient identification information and the transferable label information;

generating a warning message and generating at least an incident report if the patient identification information does not correspond to the transferable label information;

scanning at least one administration identification device with the data collection unit, further adapted to obtain administration identification information, within a pre-determined amount of time of scanning the patient identification device and communication the administration identification information to the computer system and denying access to the patient medical history file if the time between the scanning patient identification device and the administration identification device exceeds the pre-determined time limit; and administering the medication if the patient identification information corresponds to the transferable label information.

* * * * *